(12) United States Patent
Cullen

(10) Patent No.: US 8,433,587 B1
(45) Date of Patent: Apr. 30, 2013

(54) COMMUNICATION OF MEDICAL PRESCRIPTIONS WITH MOBILE PROCESSING SYSTEMS

(75) Inventor: Mark Cullen, San Francisco, CA (US)

(73) Assignee: Remscripts, LLC, San Francisco, CA (US)

( * ) Notice: Subject to any disclaimer, the term of this patent is extended or adjusted under 35 U.S.C. 154(b) by 604 days.

(21) Appl. No.: 12/406,427

(22) Filed: Mar. 18, 2009

Related U.S. Application Data

(60) Provisional application No. 61/095,919, filed on Sep. 10, 2008.

(51) Int. Cl.
*G06F 19/00* (2011.01)

(52) U.S. Cl.
USPC .................................................. 705/3

(58) Field of Classification Search .................. 705/2, 3; 455/445, 557
See application file for complete search history.

(56) References Cited

U.S. PATENT DOCUMENTS

| | | | |
|---|---|---|---|
| 7,286,996 B1* | 10/2007 | Fiedotin et al. | 705/2 |
| 2002/0052762 A1* | 5/2002 | Kobylevsky et al. | 705/2 |
| 2004/0087336 A1* | 5/2004 | Payrits et al. | 455/557 |
| 2005/0260993 A1* | 11/2005 | Lovell, Jr. | 455/445 |
| 2009/0198510 A1* | 8/2009 | Ditto | 705/2 |

* cited by examiner

*Primary Examiner* — John Pauls
(74) *Attorney, Agent, or Firm* — Schwegman Lundberg & Woessner, P.A.

(57) ABSTRACT

In an embodiment, a method is provided for communicating a medical prescription with a mobile processing system. In this method, a first request to fulfill the medical prescription is received from the mobile processing system. This first request is formatted in an instant messaging protocol and includes a mobile processing system identifier and a transaction identifier. A patient identifier that is associated with the mobile processing system identifier is identified, and transactions associated with the patient identifier are accessed to identify a transaction that is associated with the transaction identifier. The transaction then is transmitted in a second request to a pharmacy system that is configured to fulfill the medical prescription.

17 Claims, 8 Drawing Sheets

COMMUNICATION OF MEDICAL PRESCRIPTIONS WITH MOBILE PROCESSING SYSTEMS

CROSS-REFERENCES TO RELATED APPLICATIONS

This application claims the benefit of U.S. Provisional Application No. 61/095,919, filed Sep. 10, 2008, the disclosure of which is incorporated herein by reference.

FIELD

The present disclosure relates generally to electronic medical prescription systems. In an embodiment, the disclosure relates to the communication of medical prescriptions with mobile processing systems.

BACKGROUND

A pharmacy is a place where medical prescriptions are sold and dispersed. To fill a medical prescription, a patient needs to visit the pharmacy and request the medical prescription. The medical prescription is usually not ready or available immediately upon request. Instead, the patient typically needs to wait for a period of time for the pharmacy to prepare the medical prescription. The wait for the medical prescription can take a long time, and the only way for the patient to check the status of his medical prescription is to ask a worker at the pharmacy for a status update. Such inquiries can be quite inconvenient for the patient—especially when the worker is busy attending to other patients. Furthermore, the patient cannot typically venture too far from the pharmacy because he may not hear a notification that his medical prescription is ready for pickup.

BRIEF DESCRIPTION OF DRAWINGS

The present disclosure is illustrated by way of example and not limitation in the figures of the accompanying drawings, in which like references indicate similar elements and in which.

DETAILED DESCRIPTION

The description that follows includes illustrative systems, methods, techniques, instruction sequences, and computing machine program products that embody the present invention. In the following description, for purposes of explanation, numerous specific details are set forth in order to provide an understanding of various embodiments of the inventive subject matter. It will be evident, however, to those skilled in the art that embodiments of the inventive subject matter may be practiced without these specific details. In general, well-known instruction instances, protocols, structures and techniques have not been shown in detail.

The embodiments of the invention described herein provide techniques for communicating messages associated with medical prescriptions. In an example, a patient can request a refill of his medical prescription through the use of text messaging with his mobile phone. As described in more detail below, a system receives this text messaging request and forwards it to a pharmacy system that can fulfill his request by, for example, placing an order at a particular pharmacy. After the pharmacy system fulfills the request, the pharmacy system may transmit a text message notification to the patient's mobile phone that the medical prescription is ready for pickup.

Figure 1:
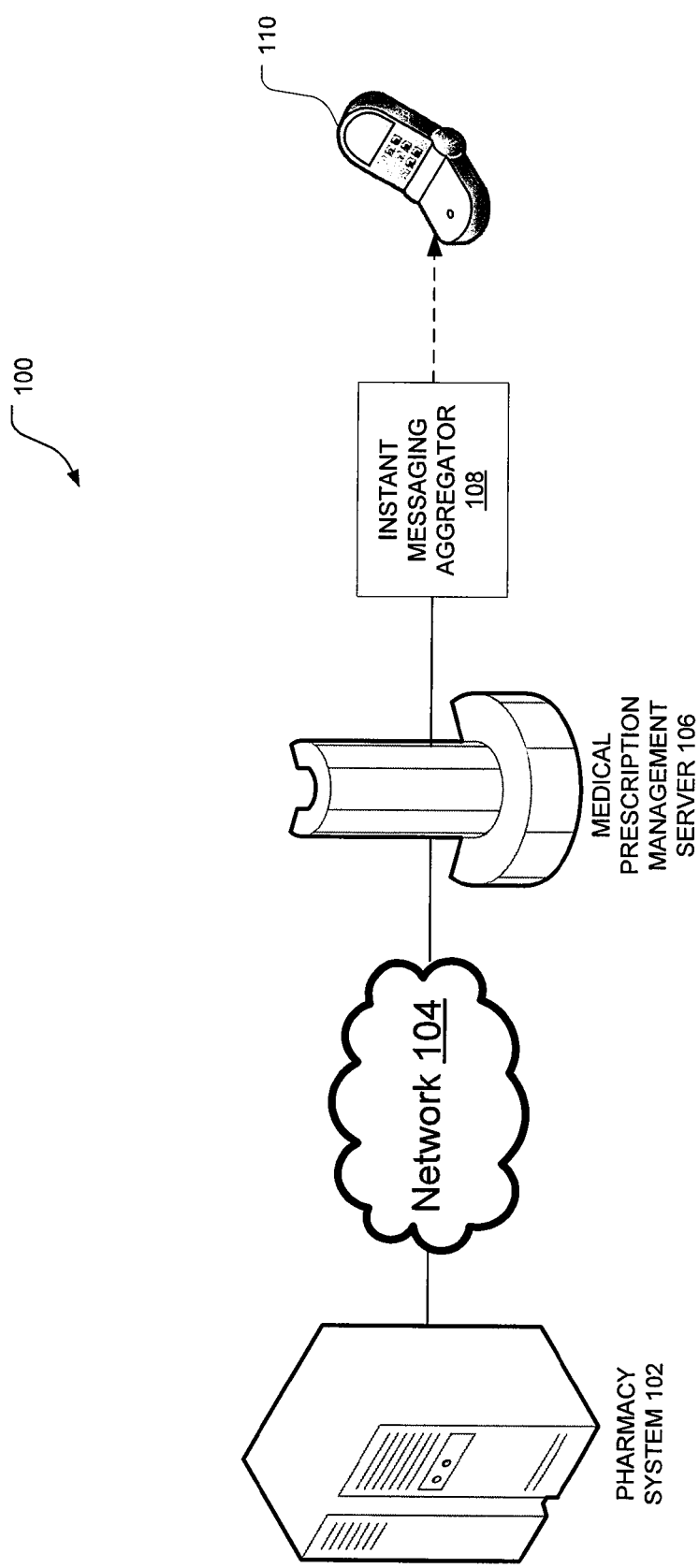
FIG. 1 depicts a diagram of a medical prescription system according to an embodiment of the invention for communicating messages regarding medical prescriptions.

FIG. 1 depicts a diagram of a medical prescription system 100 according to an embodiment of the invention for communicating messages regarding medical prescriptions. The medical prescription system 100 includes a pharmacy system 102, a medical prescription management server 106, an instant messaging aggregator 108, and a mobile processing system 110. The pharmacy system 102 is in communication with the medical prescription management server 106 by way of a network 104. It should be appreciated that the network 104 is a collection of interconnected processing systems that communicate using wired or wireless mediums. Examples of networks, such as the network 104, include Local Area Networks (LAN) and/or Wide Area Networks (WANs), such as the Internet.

Embodiments of the invention allow a patient (or any user) to manage and communicate his medical prescriptions through the use of the mobile processing system 110. It should be noted that a "mobile processing system" 110, as used herein, refers to a small or pocket-sized computing device, which may include a system battery that is used to power the mobile processing system. Examples of mobile processing systems, such as the mobile processing system 110, include a mobile phone (or smart phone), a personal digital assistant, and a laptop computer.

The management and communication of medical prescriptions include, for example, a patient using the mobile processing system 110 to submit requests to the pharmacy system 102 to fulfill medical prescriptions. The requests may be transmitted by way of text messages where such messages are formatted in instant messaging protocol. An "instant messaging protocol," refers to a communication protocol used in real-time text-based communication. Examples of instant messaging protocols include Short Message Service (SMS) protocol, Session Initiation Protocol (SIP), Extensible Messaging and Presence Protocol (XMPP), and Internet Relay Chat (IRC) protocol.

In an embodiment, the medical prescription management server 106 may communicate with the mobile processing system 110 by way of the instant messaging aggregator 108.

An "instant messaging aggregator" 108 refers to a service that is configured to convert or format messages to mobile network messages or vice versa, thereby allowing the medical prescription management server 106 to communicate with the mobile processing system 110. As an example, the instant messaging aggregator 108 may format hypertext transfer protocol (HTTP) messages from the medical prescription management server 106 to instant messaging protocol messages and vice versa. In an alternate embodiment, the medical prescription management server 106 can also format messages in the instant messaging protocol and thereby directly communicate with the mobile processing system 110 without using the instant messaging aggregator 108.

Still referring to FIG. 1, the medical prescription management server 106 may, for example, be an application server that is configured to receive requests to fulfill medical prescriptions from the mobile processing system 110 and, as explained in more detail below, to validate and forward the requests to the pharmacy system 102. The pharmacy system 102 is a system or service that manages and/or processes the fulfillment of medical prescriptions. For example, the pharmacy system may be a pharmacy management system embodied in an application server that serves a chain of pharmacies to manage inventories, to fulfill medical prescriptions, and to manage workflows. Upon receipt of a request to fulfill a medical prescription, this pharmacy system 102 can check the inventories of individual pharmacies for that particular medical prescription. If that medical prescription is available, the pharmacy system 102 may then transmit a message to the pharmacy to fill or refill that medical prescription.

After the pharmacy system 102 has fulfilled the medical prescription, it may also send a message to the mobile processing system 110 by way of the medical prescription management server 106 notifying the patient that, for example, the prescription is ready for pickup. The medical prescription management server 106 receives this message from the pharmacy system 102 and transmits this message to the mobile processing system 110 as a text message by way of the instant messaging aggregator 108.

Figure 2:
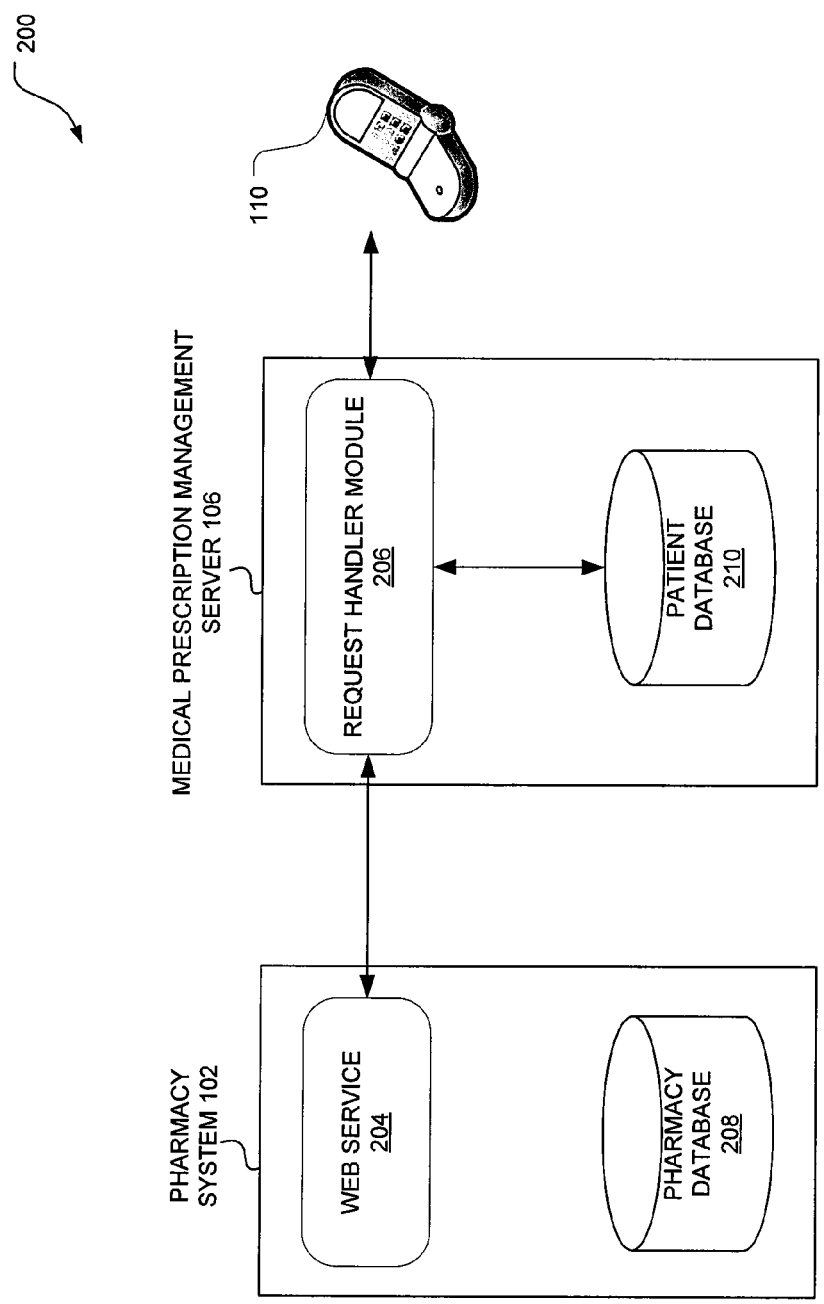
FIG. 2 depicts a block diagram of modules, in accordance with an embodiment, included in the pharmacy system and the medical prescription management server.

FIG. 2 depicts a block diagram of modules, in accordance with an embodiment, included in the pharmacy system 102 and the medical prescription management server 106. The medical prescription system 200 depicted in FIG. 2 includes the pharmacy system 102, the medical prescription management server 106, and the mobile processing system 110. As discussed previously, the mobile processing system 110 is in communication with the medical prescription management server 106, and the medical prescription management server 106 is in communication with the pharmacy system 102.

Both the pharmacy system 102 and the medical prescription management server 106 execute operating systems that manage the software processes and/or services executing on the pharmacy system 102 and the medical prescription management server 106, respectively. As depicted in FIG. 2, these software processes and/or services may include a Web service 204 and a request handler module 206. The Web service 204 is a software system configured to support interoperable machine-to-machine interaction over a network. The pharmacy system 102 communicates with the medical prescription management server 106 by way of the Web service 204. The pharmacy system 102 also includes a pharmacy database 208 that may store information related to the management of medical prescriptions, such as inventories of medical prescriptions.

On the mobile processing system 110, the request handler module 206 is configured to facilitate communication between the pharmacy system 102 and the mobile processing system 110. For example, as explained in more detail below, the request handler module 206 can handle requests to fulfill medical prescriptions from the mobile processing system 110 and to transmit these requests to the pharmacy system 102. In another example, the request handler module 206 can also handle messages transmitted from the pharmacy system 102 to the mobile processing system 110.

In addition to facilitating communication, the request handler module 206 also has access to a patient database 210, which is a data structure that stores patient information. As used herein, "patient information" refers to any suitable information that can be associated with a patient. Examples of patient information include patients' phone numbers, patients' addresses, patients' preferred pharmacies (e.g., stored as store identifiers), patients' medical prescriptions, patients' reminder schedules, and other patient related information. As described in more detail below, the request handler module 206 may use the patient information to validate and process messages transmitted between the pharmacy system 102 and the mobile processing system 110.

It should be appreciated that the request handler module 206 may be deployed in a variety of different processing systems, such personal computers, laptops computers, the medical prescription management server 106, and other processing systems. In various embodiments, such a processing system may be used to implement computer programs, logic, applications, methods, processes, or software. In other embodiments, the medical prescription management server 106 may include fewer, more, or different modules apart from those shown in FIG. 2. For example, in another embodiment, the request handler module 206 may be embodied as two or more separate modules.

Figure 3:
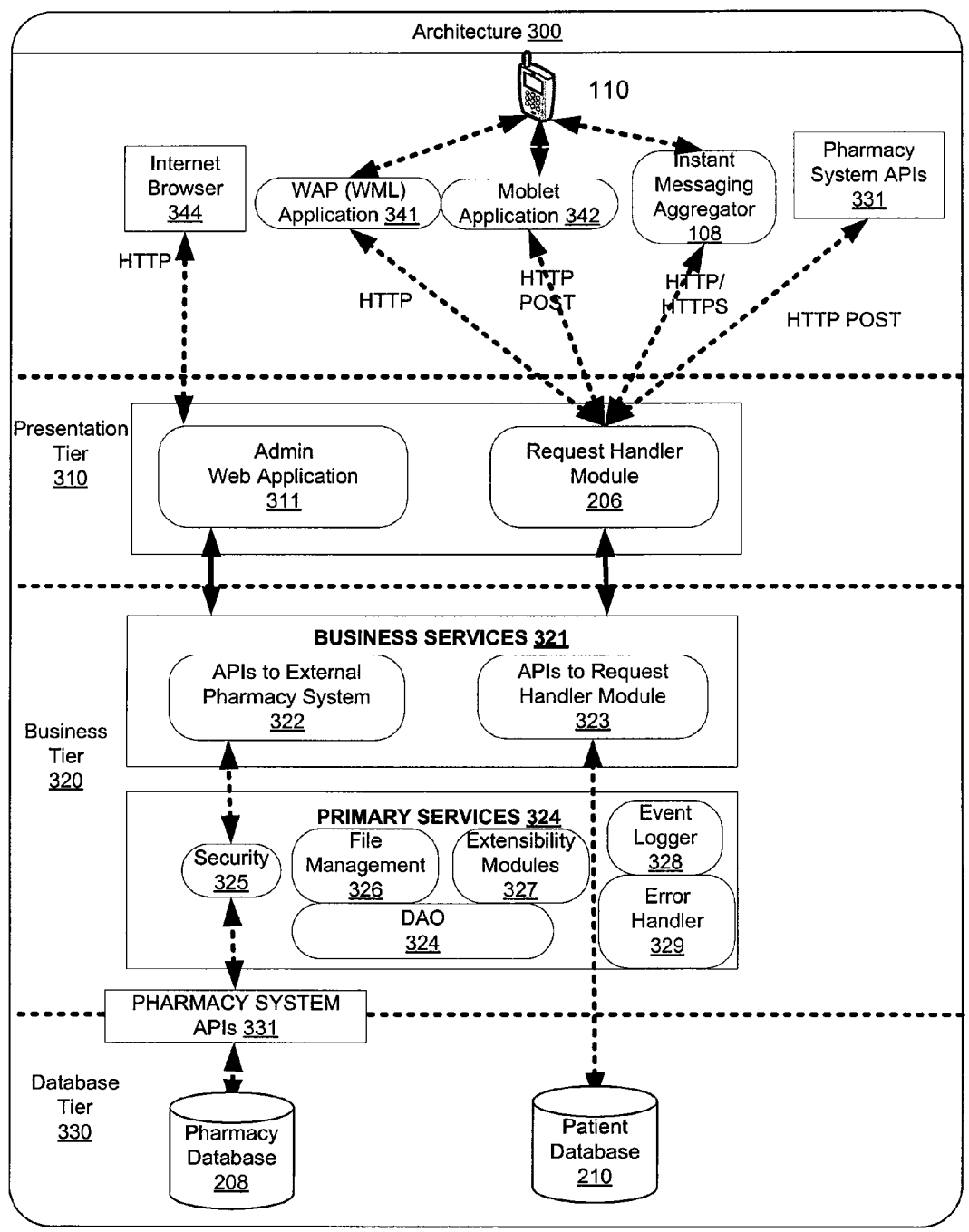
FIG. 3 depicts a block diagram of a high-level architecture of medical prescription related modules, in accordance with an embodiment, for communicating medical prescriptions with a mobile processing system.

FIG. 3 depicts a block diagram of a high-level architecture 300 of medical prescription related modules, in accordance with an embodiment, for communicating medical prescriptions with a mobile processing system 110. As depicted in FIG. 3, the architecture 300 may be divided into a presentation tier 310, a business tier 320, and a database tier 330. The database tier 330 encompasses a relational database management system with objects such as database tables, stored procedures, and data stored in the database tables. In the example of FIG. 3, the two database instances are the pharmacy database 208 and the patient database 210, which are discussed above.

The business tier 320 generally provides interface for accessing business level operations and, in an example, may be further divided into a business services sub-layer 321 and a primary services sub-layer 324. The business services sub-layer 321 is the application programming interface (API) for the presentation tier 310, and may be invoked by the presentation tier 310 to initiate a business-related request. The business services sub-layer 321 may include application programming interfaces 322 to an external pharmacy system and application programming interfaces 323 to the request handler module 206. The application programming interfaces 322 include business logic interfaces to servlets (e.g., presentation tier 310) and function to, for example, parse the input Extensible Markup Language (XML) requests to extract particular parameters. The application programming interfaces 322 may also function to call to the data access object (DAO) methods to access data from the pharmacy database 208 by way of pharmacy system application programming interfaces 331, and may also return XML responses back to the servlets. Similar to the application programming interfaces 322, the application programming interfaces 323 also include business logic interfaces to the servlets, but have the functionality to call the data access object methods that access data from the patient database 210.

The primary services sub-layer 324 provides common services to the business services sub-layer 321 and may include, for example, a security module 325, a file management module 326, data access objects 324, extensibility modules 327, an event logger 328, and an error handler 329. The security module 325 handles security-related operations (e.g., authentication and authorization). The file management module 326 is configured to manage files (e.g., create or delete directories). The extensibility modules 327 are extensions of existing modules. The event logger 328 logs events, and the error handler 329 handles errors. The data access objects 324 generally form the database services tier of the application. The basic functionalities of the data access objects 324 include, for example, exposing defined methods to the business logic modules, performing database operations, and returning the requested output objects to the calling business logic modules. It should be appreciated that the business services sub-layer 321 and the primary services sub-layer 324 may be, for example, encapsulated in an archive file and made accessible to all the modules discussed above as a library reference.

The presentation tier 310 generally functions to interface with patients by displaying data (e.g., HyperText Markup Language (HTML) or Wireless Markup Language (WML)) and/or by communicating the data (e.g., Moblet or SMS). For example, the presentation tier 310 can receive requests from the mobile processing system 110 and call the business tier 320 for operations. The presentation tier 310 may be, for example, a Web server project deployed on an application server. As depicted in FIG. 3, the presentation tier 310 may include an administrative Web application 311 and a request handler module 206. The administrative web application 311 is configured to handle specific patient requests and responses by providing data in HTML format for the Internet Web browser 344.

Similarly, the request handler module 206 is configured to handle specific patient requests and responses by providing data in, for example, WML format for an Wireless Application Protocol (WAP) or WML application 341 (e.g., a browser) on the mobile processing system 110. Additionally, the request handler module 206 can format data in the particular request/response format for a Moblet application 342 on the mobile processing system 110. The Moblet application 342 is executed on the mobile processing system 110 and provides, for example, an interface for a user to input and to receive information about his medical prescription. As an example, the Moblet application 342 can provide a graphical user interface (GUI) that displays information related to the user's medical prescription. The Moblet application 342 can also receive input from the user, format this input in an instant messaging protocol, and transmit this formatted input in the form of, for example, a request to fulfill a medical prescription. The Moblet application 342 may be based on, for example, Java 2 Platform, Micro Edition (J2ME), ANDROID operating system, Binary Runtime Environment for Wireless (BREW), and Research in Motion (RIM).

The request handler module 206 can also communicate with the mobile processing system 110 by way of the instant messaging aggregator 108, as discussed above, and also communicate with a pharmacy system by way of application programming interfaces 331 provided by the pharmacy system. As explained in more detail below, in addition to interfacing with the mobile processing system 110, the request handler module 206 can also validate requests submitted by the mobile processing system 110.

Figure 4:
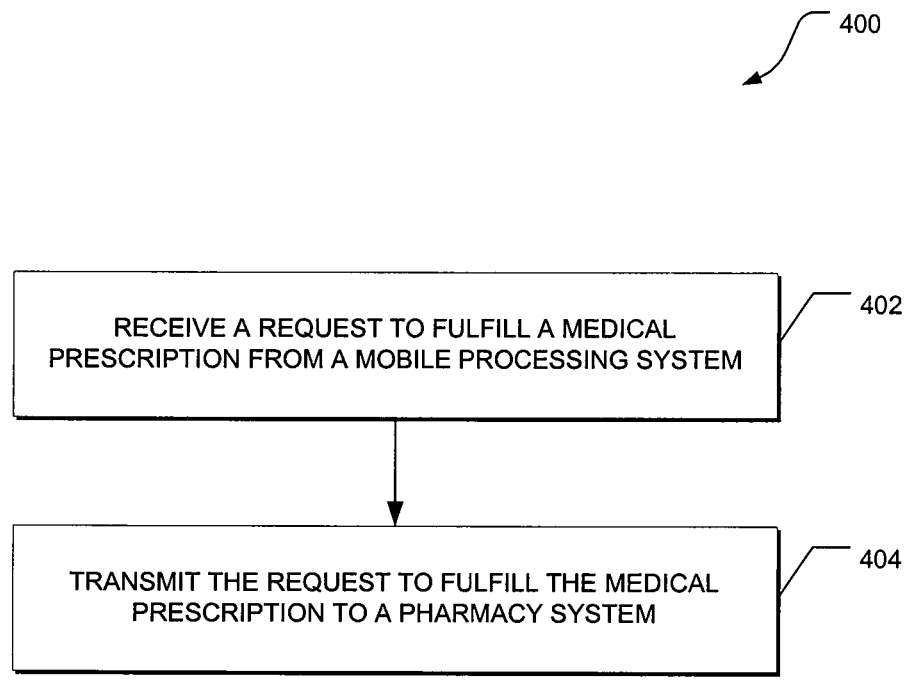
FIG. 4 depicts a flow diagram of a general overview of a method, in accordance with an embodiment, for communicating a request for medical prescription from a mobile processing system.

FIG. 4 depicts a flow diagram of a general overview of a method 400, in accordance with an embodiment, for communicating a request for medical prescription from a mobile processing system. In this embodiment, the method 400 may be implemented by the request handler module 206 and employed in the medical prescription management server 106 depicted in FIG. 2. In the method 400 of FIG. 4, the request handler module receives a request at 402 to fulfill a medical prescription from a mobile processing system. A patient may, for example, input his request for a particular prescription drug using his mobile processing system, which transmits that request to the request handler module in the form of a text message.

Upon receipt of the request, the request handler module then transmits or forwards the request at 404 to a pharmacy system that is configured to fulfill the medical prescription. As discussed in more detail below, the request handler module may also validate the request received from the mobile processing system before transmitting the request to the pharmacy system.

Figure 5:
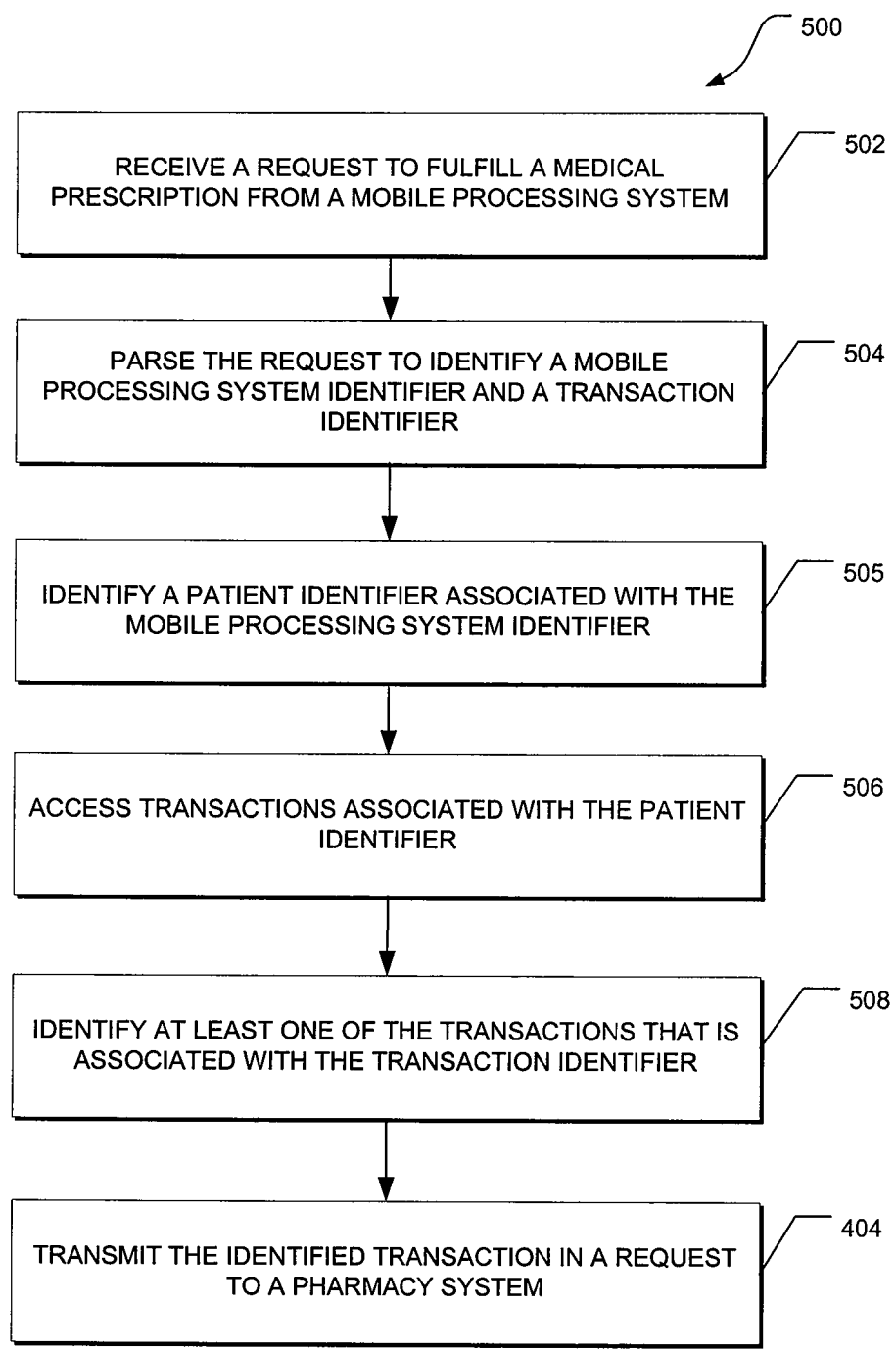
FIG. 5 depicts a flow diagram of a detailed method according to an alternate embodiment for communicating a medical prescription from a mobile processing system.

FIG. 5 depicts a flow diagram of a detailed method 500 according to an alternate embodiment for communicating a medical prescription from a mobile processing system. In this embodiment, the method 500 may be implemented by the request handler module 206 and employed in the medical prescription management server 106 depicted in FIG. 2. As depicted in FIG. 5, the request handler module receives a request to fulfill the medical prescription from a mobile processing system at 502 and parses the request at 504 to identify a mobile processing system identifier and a transaction identifier. A "mobile processing system identifier," as used herein, refers to a value (numeric and/or textual) that uniquely identifies one or more mobile processing systems. A phone number is an example of a mobile processing system identifier. Another example of a mobile processing system identifier is an International Mobile Equipment Identifier (IMEI).

It should be appreciated that a transaction refers to an interaction associated with a fulfillment of a medical prescription. Examples of transactions include requests for a particular medical prescription, requests for multiple medical prescriptions, requests for reminders to fill or refill medical prescriptions, and other transactions. A "transaction identifier," as used herein, refers to a value (numeric and/or textual) that uniquely identifies one or more transactions. An example of a value that may be used as a transaction identifier is a Common Short Code (CSC) used in text messaging. It should be appreciated that Common Short Codes are short numeric codes (e.g., five-digit or six-digit numbers) that are transmitted from a mobile processing system and, as explained in more detail below, such Common Short Codes can be assigned or allocated to uniquely identify particular transactions.

In the embodiment of FIG. 5, the request handler module first validates the request before transmitting it to a pharmacy system. As depicted at 505, the validation may include the identification of a patient identifier associated with the mobile processing system. That is, the request handler module verifies that the mobile processing system matches to a patient. In particular, the request handler module may identify the association by first accessing a data structure that stores a list of patient identifiers, a list of mobile processing system identifiers, and associations between each patient identifier and each mobile processing system identifier. As an example, the data structure may be a lookup table where the patient identifiers and the mobile processing system identifiers are stored as patient identifier/mobile processing system identifier pairs. The following Table A illustrates an example of such a data structure:

TABLE A

| Mobile Processing System Identifiers (Phone Number) | Patient Identifiers (Patient Name) |
|---|---|
| (650) 223-9002 | John Doe |
| (408) 342-3241 | Jonathan Hirsh |
| (780) 234-3421 | Jane Stevens |

A match of the mobile processing system identifier received from the mobile processing system with one of the mobile processing system identifier in the list is identified. The patient identifier that is associated with the matched mobile processing system identifier can therefore be identified from the data structure based on their association (pairings).

After the patient identifier is identified, the request handler module, in an embodiment, can access transactions that are associated with the patient identifier at 506. Each patient identifier is associated with one or more transactions. It should be noted that medical prescriptions are unique to each individual patient. For example, one patient may have a medical prescription for drugs A, B, and C while another patient may have a medical prescription for drugs C an D. As a result, each patient may have a unique set of associated transactions.

The transactions associated with each patient identifier are also stored in a data structure, which can be the same data structure that stores the list of patient identifiers and their associated mobile processing system identifiers, as discussed above. At 506, the transactions are accessed to identify, at 508, at least one transaction that is associated with the received transaction identifier. For example, the request handler module may identify the transaction by first accessing a data structure that is configured to store a list of transactions, transaction identifiers, and associations between the transactions and the transaction identifiers. Similar to the data structure discussed above, this other data structure may be a lookup table where the transactions and their transaction identifiers are stored as transaction identifier/transaction pairs. The following Table B illustrates an example of such a data structure:

TABLE B

| Patient Identifiers (Patient Name) | Transaction Identifiers (Common Short Code) | Transactions |
|---|---|---|
| John Doe | 11234 | Request Drug A |
| John Doe | 32452 | Request Drug B |
| John Doe | 23425 | Request Drugs A and B |
| Jane Stevens | 11234 | Request Drug R |
| Jane Stevens | 32452 | Request Drug Y |

A match of the transaction identifier embedded in the request from the mobile processing system with one of the transactions in the list is identified. The transaction that is associated with the matched transaction identifier can then be identified from the data structure based on their association. After the transactions are identified, the request handler module then transmits the identified transactions in a request to a pharmacy system at 510.

As an illustrative example, in reference to Tables A and B, a list of Common Short Codes "11234," "32452," and "23425" (as depicted in Table B) are allocated for identifying transactions. This list of Common Short Codes can be displayed at a mobile processing system for selection. A patient using the mobile processing system selects or inputs the Common Short Code "11234" to fulfill a medical prescription. In turn, the request handler module receives a request from a mobile phone that includes a mobile processing system identifier and a transaction identifier. The request handler module parses this request to extract a mobile processing system identifier of "(650) 223-9002" and a transaction identifier of "11234." From Table A, the request handler module identifies that the patient identifier "John Doe" is associated with the mobile processing system identifier of "(650) 223-9002." The request handler module then accesses Table B, which is configured to store the transactions associated with the patient identifier "John Doe" (as well as other patient identifiers), and identifies from Table B that the transaction "Request Drug A" is associated with the transaction identifier "11234." This transaction "Request Drug A" is then transmitted in a request to the pharmacy system.

Figure 6:
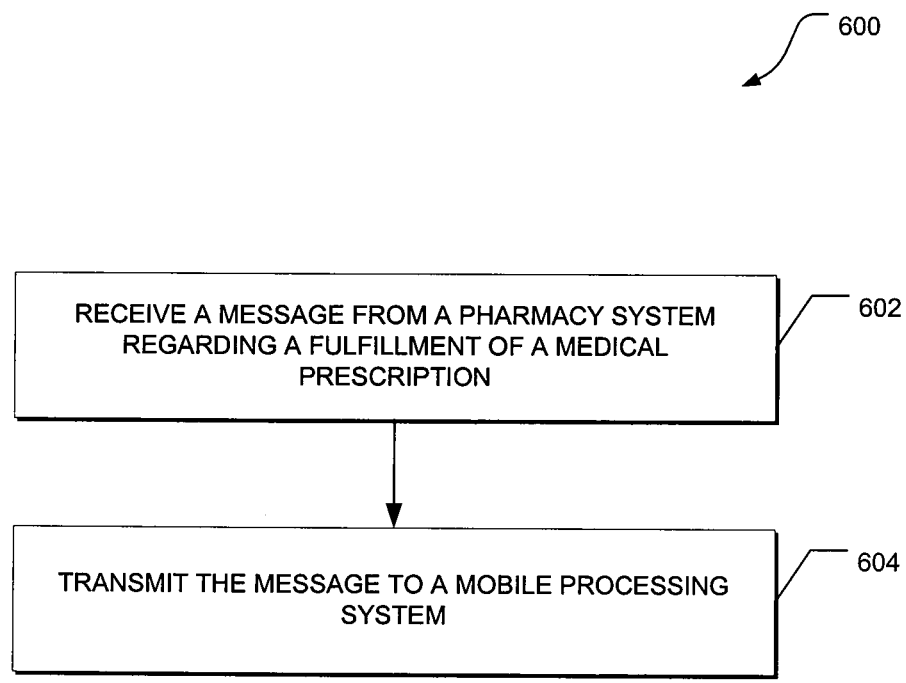
FIG. 6 depicts a flow diagram of a general overview of a method, in accordance with an embodiment, for notifying a patient the status of a medical prescription.

FIG. 6 depicts a flow diagram of a general overview of a method 600, in accordance with an embodiment, for notifying a patient the status of a medical prescription. In an embodiment, the method 600 may be implemented by the request handler module 206 and employed in the medical prescription management server 106 of FIG. 2. As depicted in FIG. 6, after a request to fulfill a medical prescription is transmitted to the pharmacy system, the request handler module may receive a message from the pharmacy system at 602 regarding a fulfillment of the medical prescription. This message can be a confirmation from them pharmacy system that the request has been received and that the medical prescription will be fulfilled. The message can also be a notification from the pharmacy system that the medical prescription is ready for pickup.

Upon receipt of the message from the pharmacy system, the request handler module then transmits the message to the mobile processing system at 604. In an embodiment, the request handler module may format the message in instant messaging protocol and directly transmit the message as a text message to the mobile processing system. In an alternate embodiment, the request handler module may transmit the message to an instant messaging aggregator, which, as discussed above, is configured to format the message in instant messaging protocol and transmit the message to the mobile processing system as a text message.

Figure 7:
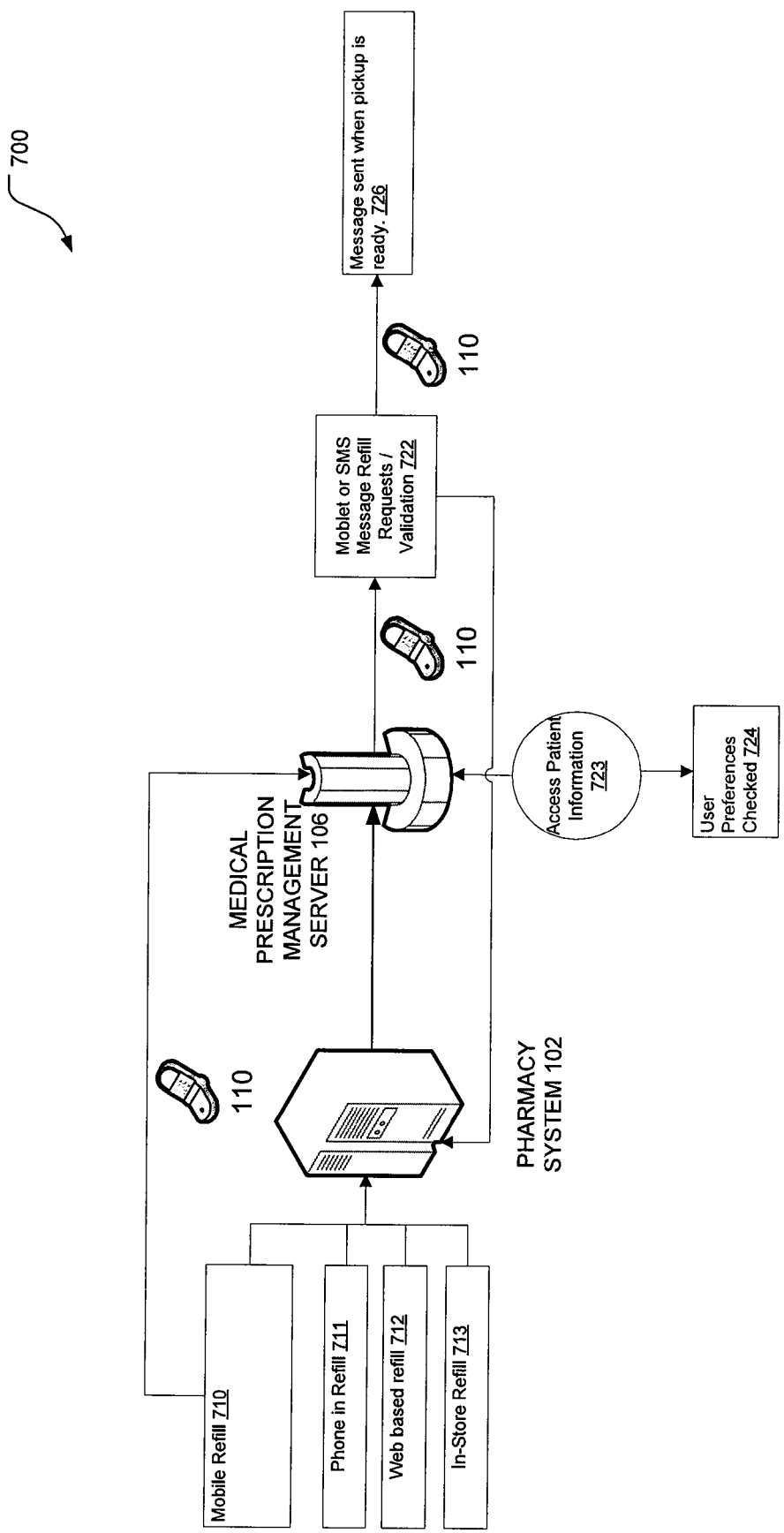
FIG. 7 depicts a combination block and flow diagram illustrating a system according with an embodiment for communicating medical prescriptions with a mobile processing system.

FIG. 7 depicts a combination block and flow diagram illustrating a system 700 according with an embodiment for communicating medical prescriptions with a mobile processing system 110. The system 700 includes a pharmacy system 102, a medical prescription management server 106, and a mobile processing system 110. As depicted in FIG. 7, a patient may use his mobile processing system 110 to submit a request to fulfill a medical prescription. As discussed above, a patient may submit the request in the form of a text message, which is received by the medical prescription management server 106. It should be noted that the patient may also alternatively submit the request directly to the pharmacy system 102 by phone 711, by Internet 712 (through use of a Web browser), or by making the request at a pharmacy store 713 where a worker at the store can input his request into the pharmacy system 102.

As depicted at 722, upon receipt of the request by way of the mobile processing system 110, the medical prescription management server 106, in an embodiment, may directly transmit or forward the request to the pharmacy system 102. In an alternate embodiment, as discussed above, the medical prescription management server 106 may validate the request first before transmitting the request to the pharmacy system 102. In addition, as depicted at 723, the medical prescription management server 106 may also access and include other patient information in the request to the pharmacy system 102. Such patient information may be relevant to fulfill the medical prescription and may be stored at the medical prescription management server 106. For example, the medical prescription management server 106 may also access and identify a patient's preferred pharmacy store, and transmit this store's identifier to the pharmacy system 102 such that the pharmacy system 102 can identify the particular pharmacy store to fulfill the medical prescription. In another example, the patient's address may also be accessed and transmitted to the pharmacy system 102 such that the pharmacy system 102 can identify stores located near the address that will be able to fulfill the medical prescription.

Upon fulfillment of the medical prescription, the pharmacy system transmits a message to the medical prescription management server 106 that, for example as depicted at 726, notifies the patient that the medical prescription is ready for pickup. In an embodiment, the medical prescription management server 106 directly transmits or forwards this message to the mobile processing system 110. In an alternate embodiment, the medical prescription management server 106 may access patient information to identify a schedule specified by the patient. This schedule may, for example, specify the times and/or dates when the patient prefers to receive messages from the medical prescription management server 106. The patient may schedule any period of time to receive the messages. For example, a patient may specify that he does not want to receive messages from 12:00 AM to 8:00 AM. As a result, the medical prescription management server checks this schedule first before sending out the message and, if the current time is between 12:00 AM to 8:00 AM, the medical prescription management server 106 will delay transmission of the message to the mobile processing system 110 until after 8:00 AM.

In a further embodiment, the schedule may be also applied to reminders from the pharmacy system 102. Here, the medical prescription management server 106 may receive requests from the pharmacy system 102 to transmit reminders to a particular patient to refill his medical prescription. Upon receipt of this request, the medical prescription management server 106 first identifies a schedule from the patient information and transmits reminders to the patient based on the schedule. For example, a patient may specify in a schedule that he only wants to receive reminders or other messages weekly. As a result, the medical prescription management server 106 transmits the reminders to the patient weekly. In another example, a patient may specify that he does not want to receive any reminders at all, at which the medical prescription management server 106 will not send any reminders to the patient even if the pharmacy system 102 makes such requests for reminders.

Figure 8:
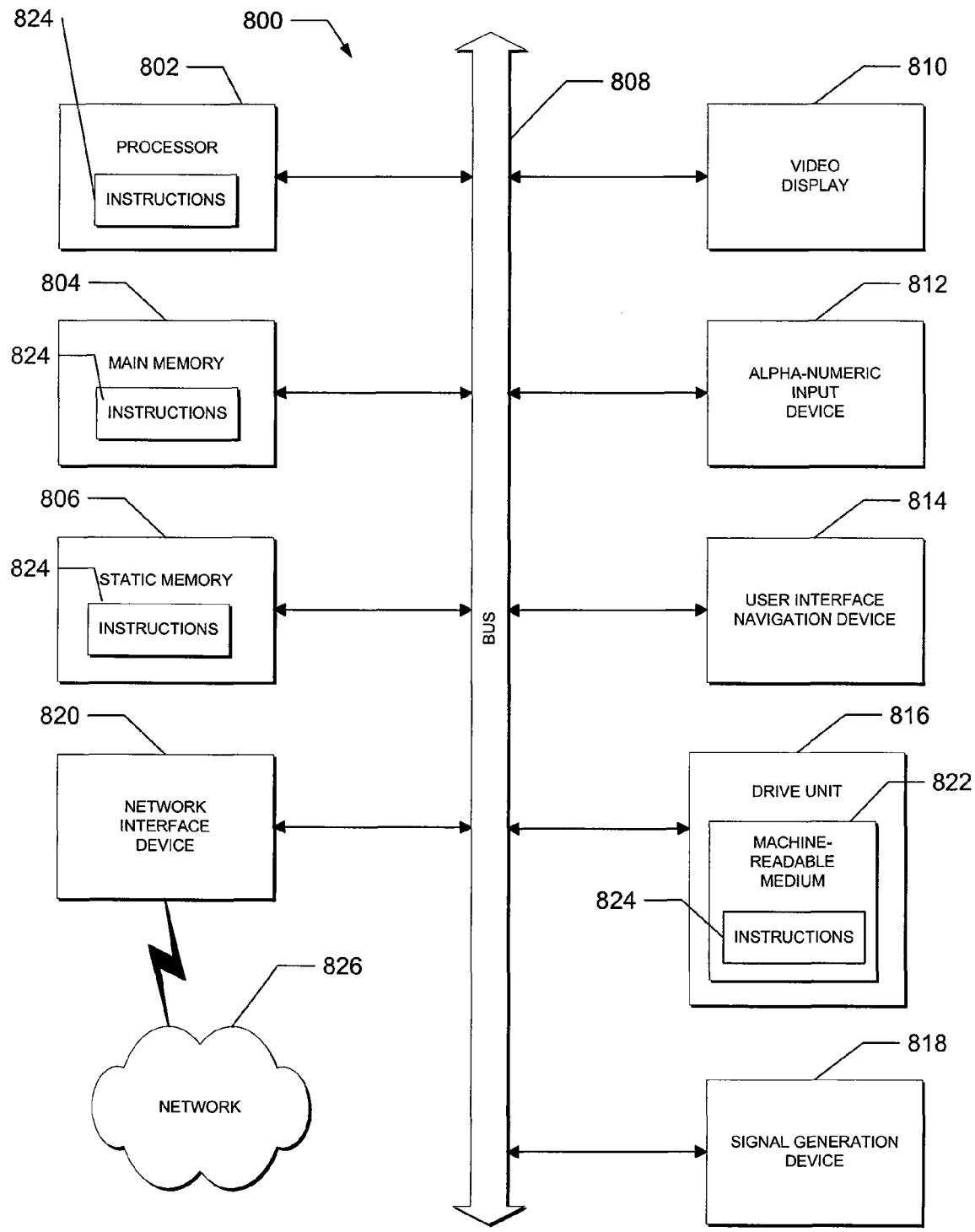
FIG. 8 depicts a block diagram of a machine in the example form of processing system within which a set of instructions, for causing the machine to perform any one or more of the methodologies discussed herein, may be executed.

FIG. 8 depicts a block diagram of a machine in the example form of processing system 800 within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. Embodiments may also, for example, be deployed by a Software-as-a-Service (SaaS), an Application Service Provider (ASP), or utility computing providers, in addition to being sold or licensed via traditional channels.

The machine is capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example processing system 800 includes a processor 802 (e.g., a central processing unit (CPU), a graphics processing unit (GPU) or both), a main memory 804, and static memory 806, which communicate with each other via bus 808. The processing system 800 may further include video display unit 810 (e.g., a plasma display, a liquid crystal display (LCD) or a cathode ray tube (CRT)). The processing system 800 also includes an alphanumeric input device 812 (e.g., a keyboard), a user interface (UI) navigation device 814 (e.g., a mouse), a disk drive unit 816, signal generation device 818 (e.g., a speaker), and network interface device 820.

The disk drive unit 816 includes machine-readable medium 822 on which is stored one or more sets of instructions and data structures (e.g., software 824) embodying or utilized by any one or more of the methodologies or functions described herein. The software 824 may also reside, completely or at least partially, within main memory 804 and/or within processor 802 during execution thereof by the processing system 800, the main memory 804, and processor 802 also constituting machine-readable, tangible media.

The software 824 may further be transmitted or received over network 826 via network interface device 820 utilizing any one of a number of well-known transfer protocols (e.g., HTTP).

While the invention(s) is (are) described with reference to various implementations and exploitations, it will be understood that these embodiments are illustrative and that the scope of the invention(s) is not limited to them. In general, techniques for communicating medical prescriptions may be implemented with facilities consistent with any hardware system or hardware systems defined herein. Many variations, modifications, additions, and improvements are possible.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the invention(s). In general, structures and functionality presented as separate components or modules in the exemplary configurations may be implemented as a combined structure or component. Similarly, structures and functionality presented as a single component may be implemented as separate components. These and other variations, modifications, additions, and improvements fall within the scope of the invention(s).

What is claimed is:

1. A method of communicating a medical prescription from a mobile processing system, the method comprising:
   receiving a first request to fulfill the medical prescription from the mobile processing system, the first request being formatted in an instant messaging protocol and including a mobile processing system identifier and a transaction identifier, the mobile processing system identifier being a phone number of the mobile processing system and the transaction identifier being in Common Short Code in the instant messaging protocol;

identifying a patient identifier that is associated with the mobile processing system identifier, the patient identifier being a patient name;

accessing a data structure that comprises a plurality of patient identifiers, a plurality of transactions associated with the plurality the patient identifiers, a plurality of transaction identifiers that are associated with the plurality of transactions, and a plurality of associations between each of the plurality of transactions and each of the plurality of transaction identifiers, each transaction being an interaction associated with a fulfillment of the medical prescription, each transaction identifier in the data structure being in the Common Short Code;

identifying, from the data structure, one or more transactions in the plurality of transactions that are associated with the transaction identifier included in the first request;

determining, based on the data structure, a patient-specific transaction from among the identified transactions, the patient-specific transaction being associated with the patient identifier corresponding to the mobile processing system identifier included in the first request; and transmitting the patient-specific transaction in a second request to a pharmacy system, the pharmacy system configured to fulfill the medical prescription.

2. The method of claim 1, further comprising:
receiving a message from the pharmacy system regarding a fulfillment of the medical prescription; and
transmitting the message to the mobile processing system, the message configured to be formatted in the instant messaging protocol.

3. The method of claim 1, further comprising:
identifying patient information associated with the patient identifier; and
transmitting the patient information with the second request to the pharmacy system.

4. The method of claim 3, wherein the patient information includes a store identifier.

5. The method of claim 1, further comprising:
receiving a third request from the pharmacy system to transmit a reminder to the mobile processing system, the reminder being a message to fulfill the medical prescription at a future date; and
transmitting the reminder to the mobile processing system.

6. The method of claim 1, wherein the mobile processing system identifier is a phone number of the mobile processing system.

7. The method of claim 1, wherein the mobile processing system is a mobile phone.

8. The method of claim 1, wherein the instant messaging protocol is a Short Message Service (SMS) protocol.

9. A non-transitory, machine-readable medium that stores instructions, which when performed by a machine, cause the machine to perform operations comprising:
receiving a message from a pharmacy system regarding a fulfillment of a medical prescription corresponding to a user;
accessing a user-specific schedule corresponding to the user, the user-specific schedule specifying at least one of a user-specified time and user-specified date when the message can be transmitted to a mobile processing system associated with the user; and
transmitting the message to the mobile processing system based on the user-specific schedule, the message configured to be formatted in an instant messaging protocol.

10. The non-transitory, machine-readable medium of claim 9, wherein the message is transmitted to the mobile processing system by way of an instant messaging aggregator, the instant messaging aggregator configured to format the message in the instant messaging protocol.

11. The non-transitory, machine-readable medium of claim 9, wherein the instructions, when performed by the machine, cause the machine to perform operations further comprising formatting the message in the instant messaging protocol.

12. The non-transitory, machine-readable medium of claim 9, wherein the message is a confirmation that the medical prescription is to be fulfilled.

13. The non-transitory, machine-readable medium of claim 9, wherein the message is a notification that the medical prescription is ready for pickup.

14. A processing system comprising:
at least one processor; and
a memory in communication with the at least one processor, the memory being configured to store a request handler module that is executable by the at least one processor, the request handler module having instructions, that when executed by the at least one processor, cause operations to be performed, the operations comprising:
receiving a Short Message Service (SMS) request from a mobile phone to fulfill a medical prescription, the SMS request including a phone number of the mobile phone and a transaction identifier in Common Short Code in the instant messaging protocol;
identifying a patient identifier that is associated with the phone number;
accessing a data structure that is configured to store a plurality of patient identifiers, a plurality of transactions associated with the plurality of patient identifiers, a plurality of transaction identifiers, and a plurality of associations between each of the plurality of transactions and each of the plurality of transaction identifiers, each transaction identifier being in Common Short Code, each transaction defining a type of medical prescription to be fulfilled;
identifying, from the data structure, a match of the transaction identifier included in the SMS request with one of the plurality of transaction identifiers;
identifying, from the data structure, one or more transactions of the plurality of transactions that are associated with the one of the plurality of transaction identifiers, based on one or more of the plurality of associations between the one or more of the plurality of transactions and the one of the plurality of transaction identifiers;
determining, based on the data structure, a patient-specific transaction from among the identified transactions, the patient-specific transaction being associated with the patient identifier corresponding to the phone number included in the SMS request;
transmitting the patient-specific transaction in a request to a pharmacy system;
receiving a message from the pharmacy system regarding a fulfillment of the medical prescription; and
transmitting the message to the mobile phone by way of a SMS aggregator, the SMS aggregator configured to format the message in SMS.

15. The processing system of claim 14, wherein the processing system is an application server.

16. The processing system of claim 14, wherein the operation of identifying the patient identifier comprises:
accessing a data structure that is configured to store a plurality of patient identifiers, a plurality of phone numbers, and a plurality of associations between each of the plurality of patient identifiers and each of the plurality of phone numbers;

identifying a match of the phone number of the mobile phone with one of the plurality of phone numbers; and identifying one of the plurality of patient identifiers that is associated with the one of the plurality of phone numbers based on one of the plurality of associations between the one of the plurality of patient identifiers and the one of the plurality of phone numbers.

17. The processing system of claim 14, wherein the operations further comprise:

receiving a further request from the pharmacy system to transmit a reminder to the mobile phone, the reminder being a further message to fulfill the medical prescription at a future date;

identifying a schedule associated with the further request; and transmitting the reminder to the mobile phone based on the schedule.

\* \* \* \* \*

UNITED STATES PATENT AND TRADEMARK OFFICE
CERTIFICATE OF CORRECTION

| | | |
|---|---|---|
| PATENT NO. | : 8,433,587 B1 | Page 1 of 1 |
| APPLICATION NO. | : 12/406427 | |
| DATED | : April 30, 2013 | |
| INVENTOR(S) | : Cullen | |

It is certified that error appears in the above-identified patent and that said Letters Patent is hereby corrected as shown below:

In the claim

Column 11, line 6, Claim 1, after "plurality", insert --of--, therefor

Signed and Sealed this
Sixth Day of October, 2015

Michelle K. Lee
*Director of the United States Patent and Trademark Office*